United States Patent [19]

Nakanishi et al.

[11] Patent Number: 4,842,595

[45] Date of Patent: Jun. 27, 1989

[54] ABSORBENT ARTICLE

[75] Inventors: Minoru Nakanishi; Akira Sakurai, both of Utsunomiya, Japan

[73] Assignee: Kao Corporation, Tokyo, Japan

[21] Appl. No.: 114,018

[22] Filed: Oct. 29, 1987

[30] Foreign Application Priority Data

Nov. 5, 1986 [JP] Japan ........................... 61-263542

[51] Int. Cl.[4] ........................................ A61F 13/16

[52] U.S. Cl. ........................................ 604/372

[58] Field of Search ............................ 604/370, 372

[56] References Cited

U.S. PATENT DOCUMENTS 3,017,291 1/1962 McLaughlin et al. ............ 604/372

3,651,809 3/1972 Champaigne .................... 604/372

3,886,942 6/1975 Bernardin .

3,901,236 8/1975 Assarsson et al. .

4,235,237 11/1980 Mesek et al. .

4,372,310 2/1983 Sergeant ........................ 604/372

*Primary Examiner*—Randall L. Green

*Attorney, Agent, or Firm*—Birch, Stewart, Kolasch & Birch

[57] ABSTRACT

An absorbent article comprises a liquid-permeable surface sheet, a liquid-impermeable leakproof sheet, and an absorbent layer provided between the two sheets, characterized in that at least part of a material constituting said absorbent layer is made of a nodular fiber, and that said nodular fiber contains a fiber having a wet to dry tenacity ratio of 80% or more.

21 Claims, 1 Drawing Sheet

1 2 7 8

ABSORBENT ARTICLE

FIELD OF INDUSTRIAL APPLICATION

The present invention relates to an absorbent article such as a sanitary napkin, a disposable diaper and a pad for incontinence.

BACKGROUND OF THE INVENTION

The present invention relates to an absorbent article, and description will hereinafter be made as regards a sanitary napkin as a representative example of the absorbent article since the same idea can basically apply to other absorbent articles.

A sanitary napkin generally utilizes, as basic constituents, three components, namely a liquid-permeable surface sheet, an absorbent layer made of fluff pulp, absorbent tissues, a water-absorbent polymer or the like, and a liquid impermeable-leakproof sheet. Recently, a sanitary napkin comprising a rayon fiber assembly (hereinafter referred to briefly as "cushioning wool") or the like provided under the surface sheet (on the absorbent layer) has been generally used.

An object of the present invention is to greatly improve the defects of the absorbent layer and cushioning wool which have been generally used in a conventional sanitary napkin or the like as described hereinbefore.

First, fluff pulp is economical, flexible and highly hydrophilic. Thus, it is widely used as the absorbent layer.

Since, however, water absorbent by a laminate of fluff pulp is nearly completed based on a retention of liquid between fibers (capillary) and the laminate has no interfiber bonding strength, it is easily deformed and capillaries formed between the fibers are broken so that liquid retained is easily released when it undergoes a compressional force. The laminate shows a little recovery from compression when it is dry, but no recovery when it contains absorbent water. This causes slippage and wilting of the absorbent layer, and hence constitutes the main cause of the occurence of leakage. The following techniques for eliminating the above-mentioned defects have been disclosed.

(1) As shown in FIG. 4, a core material 4 having a shape retention property, such as a foam, is provided in the absorbent layer 3 or on the side of the non-effective surface to prevent the deformation of the absorbent article (see Japanese Utility Model Laid-Open No. 6,099/1981)

(2) As shown in FIG. 6, the absorbent layer itself is replaced with an elastic porous material 5 (e.g., a urethane skeleton foam, a polyester fiber assembly having fibers bonded with a binder, or the like) (see Japanese Patent Laid-Open No. 22,354/1986).

In the case of (1), however, although the shape retention property of the construction as a whole can be maintained, when the absorbent layer itself is deformed slippage and wilting are caused as shown in FIG. 5.

In the case of (2), although the recovery from deformation of the absorbent article is excellent, the hydrophilic nature of the elastic porous material is so extremely poor as compared with the fluff pulp that the material is not sufficient in liquid uptake capacity and liquid retention.

Since a cushioning wool 6 as shown in FIG. 7 is used mainly for the purpose of effectively absorbing a liquid excreted on the surface sheet 1 in the inside and causing the liquid to migrate into the absorbent layer 3, it is generally made of rayon fiber (occasionally pulp). When the amount of excretion is relatively small, it is very effective. In contrast, when the amount of excretion is large, the cushioning wool wilts due to its highly hydrophilic nature just as in the case of the above mentioned fluff pulp. As a result, a layer having a large amount of a liquid absorbed therein is formed between the absorbent layer 3 and the surface sheet 1, and the liquid readily flows back to the surface sheet, thus leading a to lowering in dryness and causing a side leak.

Various improvements of these defects have been proposed. For example, a method has been proposed to use a synthetic fiber instead of a rayon fiber, and another method use a fiber assembly (tow). Since the synthetic fiber and the fiber assembly both have a low hydrophilic nature, however, uptake of a liquid from a surface sheet is insufficient, and the liquid inevitably diffuses between the surface sheet and the cushioning wool, thereby causing poor dryness and a side leak.

Since no sufficient improvement in the resistance to compression is attained as well, no improvement is made as regards prevention of the ready back flow of a liquid under a pressure in the direction of compression due to wearing.

BRIEF DESCRIPTION OF THE INVENTION

The invention of the present ivention have made intensive investigations with a view to solving the above-mentioned problems and, as a result, have completed the present invention.

Specifically, the present invention provides an absorbent article comprising a liquid-permeable surface sheet, a liquid-impermeable leakproof sheet, and an absorbent layer provided between the two sheets, characterized in that at least part of a material constituting the absorbent layer is made of a nodular fiber and that the nodular fiber contains a fiber having a wet to dry tenacity ration of 80% or more.

BRIEF DESCRIPTION OF THE DRAWINGS:

FIG. 1 is an example of a sanitary napkin comprising nodular fiber in the upper FIG. 1 is an example of a sanitary napkin comprising nodular fiber in the upper portion of the absorbent layer, FIG. 2 is an example of a sanitary napkin comprising a nodular fiber provided in the whole of the absorbent layer, and FIG. 3 is an example of a sanitary napkin having an absorbent layer constituted only of a nodular fiber.

Figure 1:
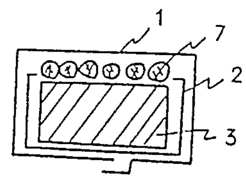
FIGS. 1 to 3 are crosssectional views of examples of the absorbent article of the present invention.

The following reference numerals are employed in the Figures:

1: liquid-permeable surface sheet
2: liquid-permeable leakproof sheet
3: absorbent layer
4: piece for shape retention
5: elastic porous material
6: rayon cushioning wool
7: nodular fiber
8: hydrophilic fiber
9: movable female waist model
10: liquid injection tube
11: test sample The wet to dry tenacity ratio as used in the present invention is a value obtained by the formula: wet/dry tenacity ratio$=(SW/SD)\times 100$, wherein SD is a tensile strength in a standard state and SW is a tensile strength in a wet state. The tensile test is made as regards a single filament in accordance with the method as stipulated in the "Tensile Strength Tests of Fibers" of JIS L 1069.

The content of the fiber having a wet to dry tenacity ratio of 80% or more in nodular fiber according to the present invention is not particularly limited, and may be chosen with due consideration given to required characteristics. However, it is preferably substantially 20 wt.% or more, and more preferably 50 wt.% or more. When the content of the fiber having a wet to dry tenacity ratio of 80% is less than 20 wt.%, no sufficient compression resistance is obtained.

Hydrophilic fiber materials can be mentioned as a fiber material contained in the nodular fiber other than the fiber material having a wet to dry tenacity ratio of 80% or more. Use of nodular fiber comprised of only a fiber material having a wet to dry tenacity ratio of 80% or more (hereinafter referred to briefly as a "skeletal fiber"), or a skeletal fiber and a hydrophilic fiber material can provide an absorbent layer which does not undergo reduction in the liquid absorption, namely hydrophilic nature, and can effectively cause a liquid to migrate into the absorbent layer, and which shows such a compression resistance that a liquid does not flow back to the surface even when a pressure is applied thereto, that is a reduced wilting tendency.

Examples of the sketetal fiber having a wet to dry tenacity ratio of 80% or more to be used in the present invention include polyester, polypropylene, polyethylene, polyvinyl chloride, polyvinylidiene chloride, nylon, acrylic, cotton, and flax fibers. Conjugate fibers composed of two components selected from among polyester, polypropylene, etc. may also be used alone or in mixture.

Among others, polyester, polyester/polypropylene conjugate and polyester/polyethylene conjugate fibers are preferred from the viewpoint of elastic recovery from compression. The fiber size is not particularly limited and may be chosen according to the required characteristics. Generally, it is preferably about 1.5 to 6 deniers. When it is less than 1.5 deniers, no sufficient compression resistance is obtained. When it is more than 6 deniers, stiffness is felt in an aspect of hand unfavorably.

Surface modification such as a treatment of the fiber surface with a lubricant or a plasma may be done without limitation in so far as the compression resistance is not affected.

Examples of the hydrophilic fiber material include rayon, cuprammonium rayon, and fluff pulp. They may be used alone or in mixture. There are no limitations in fiber lenght and fiber size.

The process for preparing a nodular fiber may comprise cutting a fiber assembly to have adequate length and width (or adequate weight as the case may be), making the cut fibers nodular, and partially fusing the skeletal fiber by heating if it is fusable, or partially bonding the fiber with a binder which can be neither swollen nor dissolved in water.

Although the size of the nodular fiber according to the present invention is not particularly limited, it usually is preferably 1 mm to 60 mm.

The methods of using such a nodular fiber as a constituent in the absorbent article of the present invention include (1) one in which it is used under the surface sheet, (2) one in which it is mixed with other hydrophilic fiber and the mixture is used in the whole of the absorbent layer, and (3) one in which the absorbent layer is constituted only of the nodular fiber. In the cases of (1) and (2), an absorbent layer using 3 to 80 wt.% of a nodular fiber based on the absorbent layer is usually suitable used. Needles to say, however, the present invention is not limited to this.

EXAMPLES

The following Examples will illustrate the present invention in more detail but they should not be construed as limiting the scope of the invention.

EXAMPLE 1

Figure 7:
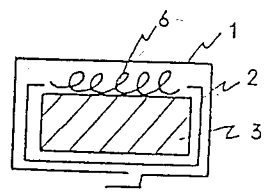
FIG. 7 is a crosssectional view of a conventional general sanitary napkin.

In this embodiment a nodular fiber was used under the surface sheet on the upper side of the absorbent layer. This embodiment is shown in FIG. 1. As a test sample a sanitary napkin is comprised of a surface sheet 1, an absorbent layer 3, a leakproof sheet 2, and cushioning wool 6 provided under the surface sheet as shown in FIG. 7.

The surface sheet used herein was a heat-bonded non-woven fabric comprised of 65% of a polyester fiber and 35% of a polyethylene/polypropylene conjugate fiber and having a base weight of 20g/m$^2$. The absorbent layer was comprised of 2 g of fluff pulp, 1.5 g of absorbent tissues, and 0.3 g of a super-absorbent polymer.

The leakproof sheet used herein was a waterproof paper (25 g/m$^2$) having a 10$\mu$-thick polyethylene film laminated thereon.

A napkin having cushioning wool 6 made of a rayon fiber was used as a comparative sample. This wool was replaced with various nodular fibers according to the present invention as shown in Table 1 to examine the effects thereof. The rayon wool 6 and the nodular fibers 7 of the present invention were each used in an amount of 0.3 g. In order to confirm the effect of the present invention, the amount of liquid back flow was measured. The results are shown in Table 2.

Measurement of amount of liquid back flow 10 g of artifical blood was injected into a test sample. The liquid, which flowed back when a pressure of 50 g/cm$^2$ was applied to the test sample, was soaked up with the fiber paper. The weight of the liquid soaked up was defined as the amount of liquid back flow.

TABLE 1

| Materials Used in Test | | | | | | |
|---|---|---|---|---|---|---|
| No. | Material | Fiber fineness (denier) | Fiber length (mm) | Extent of crimping | wet/dry tenacity ratio (1) (%) |
| a | rayon | 3 | 15 | small | 60–65 |
| b | rayon | 6 | 15 | small | 60–65 |
| c | rayon | 3 | 38 | small | 60–65 |
| d | cottony pulp | — | 1–2 | — | — |
| e | dewaxed cotton | — | — | — | — |
| f | polyester | 1.5 | 38 | large | 100 |
| g | polyester | 3 | 38 | medium | 100 |
| h | polyester | 6 | 51 | medium | 100 |
| i | polypropylene | 1.5 | 38 | medium | 100 |
| j | polypropylene | 3 | 38 | medium | 100 |
| k | polypropylene | 6 | 51 | large | 100 |
| l | polyethylene/ polypropylene conjugate fiber | 3 | 38 | medium | 100 |
| m | polyethylene/ polyester conjugate fiber | 3 | 38 | medium | 100 |

Note:
(1) A tensile strength test of a single filament was conducted in accordance with the method as stipulated in the "Tensile Strength Tests of Fibers" of JIS L 1069. The wet to dry tenacity ratio was obtained by the following equation: wet/dry tenacity ratio (%) = (SW/SD) × 100 wherein SD is a tensile strength in a standard state and SW is a tensile strength in a wet state.

as stipulated in the "Tensile Strength Tests of Fibers" of JIS L 1069. The wet to dry tenacity ratio was obtained by the following equation: wet/dry tenacity ratio (%)=(SW/SD)×100 wherein SD is a tensile strength in a standard state and SW is a tensile strength in a wet state.

TABLE 2

| Sample No. | Material | Blending weight ratio | Shape | Amount of liquid back flow (g) | Remarks |
|---|---|---|---|---|---|
| 1-1 | f | 100 | sphere | 1.4 | present invention |
| 1-2 | g | " | " | 1.2 | |
| 1-3 | h | " | " | 1.1 | |
| 1-4 | i | " | " | 1.7 | |
| 1-5 | j | " | " | 1.5 | |
| 1-6 | k | " | " | 1.4 | |
| 1-7 | l | " | " | 1.6 | |
| 1-8 | m | " | " | 1.4 | |
| 1-9 | f/a | 60/40 | " | 1.1 | |
| 1-10 | l/e | 80/20 | " | 0.9 | |
| 1-11 | m/d | 70/30 | " | 0.9 | |
| 1-12 | a | 100 | staple | 2.3 | comparative |
| 1-13 | c | " | " | 2.5 | |
| 1-14 | e | " | " | 2.2 | |

EXAMPLE 2

Figure 2:
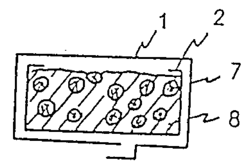

In this embodiment a nodular fiber was used throughout the whole of the absorbent layer. This embodiment is shown in FIG. 2.

The surface sheet 1 and the leakproof sheet used herein were the same as those used in Example 1. The absorbent layer was a mixture of 0.3 g of a water-absorbent polymer and 3.5 g of a mixture of a nodluar fiber 7 and a hydropilic fiber 8 such as fluff pulp, rayon or cotton. Samples thus obtained are shown in Table 3.

TABLE 3

| Sample No. | Material of nodular fiber (wt. %) | | Material of hydrophilic fiber (wt. %) | |
|---|---|---|---|---|
| 2-1 | g | 70 | d | 30 |
| 2-2 | h | 60 | c | 40 |
| 2-3 | l | 60 | e | 40 |
| 2-4 | m | 50 | d | 50 |
| 2-5 | 1/c(60-40) | 60 | d | 40 |

EXAMPLE 3

Figure 3:
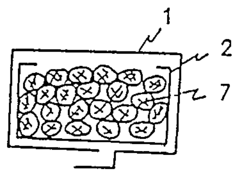
Figure 4:
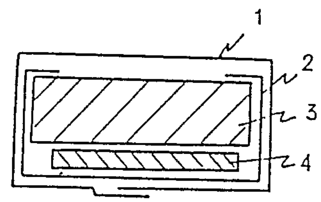
FIG. 4 is a crosssectional view of a conventional sanitary napkin having a piece for shape reteñtion.
Figure 5:
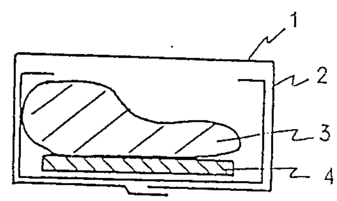
FIG. 5 is a crosssectional view of this sanitary napkin having the piece for shape retention when the absorbent layer is deformed.
Figure 6:
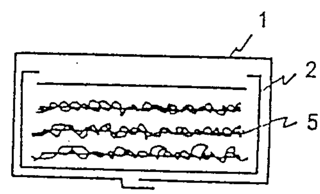
FIG. 6 is a crosssectional view of a conventional sanitary napkin having an absorbent layer using an elastic porous material.

In this embodiment the absorbent layer constituted only a nodular fiber. This embodiment is shown in FIG. 3.

The surface sheet 1 and the leakproof sheet 2 used herein were the same as those used in Example 1. The absorbent layer was a mixtue of 3.5 g of a nodular fiber 7 and 0.3 g of a water-absorbent polymer. A mixture or a lamination of nodular fibers constituted of different materials were also made.

TABLE 4

| Sample No. | Nodular fiber (1) | wt % | (2) | wt % | (3) | wt % | Remarks |
|---|---|---|---|---|---|---|---|
| 3-1 | 1/c(60/40) | 100 | — | | — | | Only a single component |
| 3-2 | m/b(80/20) | 30 | 1/c(50/50) | 70 | — | | mixture of two components |
| 3-3 | h/b(80/20) | 30 | m/c(50/50) | 70 | — | | laminate of (1) and (2), (1) being provided on the side of surface sheet |
| 3-4 | m/b(90/10) | 10 | 1/c(70/30) | 30 | 1/c(50/50) | 60 | laminate of (1), (2) and (3) in this order, (1) being provided on the side of surface sheet |

TEST EXAMPLE 1

In order to confirm the effects of these samples, the amount of liquid back flow and the amount of dynamic maxium absorption were measured.

The results are shown in Table 5.

Measurement of amount of liquid back flow

The same method as in Example 1 was used.

Measurement of amount of dynamic maximum absorption

Figure 8:
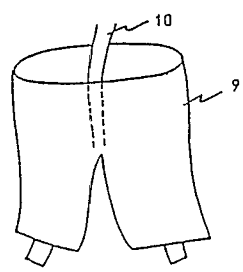
FIG. 8 is a perspective view of a movable female waist model.
Figure 9:
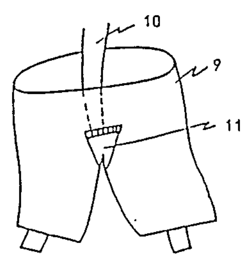
FIG. 9 is a perspective view showing the state of a test sample worn on the movable female waist model.

A test sample 11 was put on a movable female waist model 9 as shown in FIG. 8 in such a way as that shown in FIG. 9. After shorts were put on, the model was set in walking movement at a rate of 50 m/min while artificial blood was injected into the test sample through a dropping tube 10. The amount of the artificial blood absorbed until side leak occurred was measured.

TABLE 5

| Sample No. | Amount of liquid back flow (g) | Maximum amount of dynamic absorption (g) | Remarks |
|---|---|---|---|
| 1-1 | 1.4 | 6.1 | present invention |
| 1-2 | 1.2 | 6.8 | present invention |
| 2-1 | 1.5 | 8.6 | present invention |
| 2-2 | 1.4 | 9.2 | present invention |
| 2-3 | 1.2 | 9.4 | present invention |
| 2-4 | 1.5 | 7.4 | present invention |
| 2-5 | 1.3 | 8.0 | present invention |
| 3-1 | 1.8 | 6.2 | present invention |
| 3-2 | 1.6 | 7.8 | present invention |
| 3-3 | 1.5 | 8.3 | present invention |
| 3-4 | 1.2 | 9.4 | present invention |
| 1-13 | 2.5 | 4.9 | comparative |

It is apparent from the above that, since the absorbent article of the present invention is excellent in compression resistance and recovery from deformation, liquid back flow to the surface (surface dryness) and the amount of dynamic absorption (leakproofness) are greatly improved as compared with that of the conventional article.

FUNCTION AND EFFECTS

The absorbent article of the present invention comprises a nodular fiber containing a skeletal fiber having a wet to dry tenacity ratio of 80% or more in at least part of the absorbent layer. Thus, a liquid can be effectively caused to migrate into the absorbent layer without reduction in the liquid absorption, namely the hydrophilic nature, of the absorbent layer. Since the absorbent layer is excellent in compression resistance and recovery from deformation even when a liquid is absorbed, the absorbent layer neither slips nor wilts when the absorbent layer is deformed, whereby liquid back flow the surface and side leakage which are mainly caused by slippage and wilting can be remarkably reduced.

What is claimed is:

1. An absorbent article comprising:

a liquid-permeable surface sheet, a liquid-permeable leakproof sheet contained within said surface sheet, and an absorbent layer disposed within said leakproof sheet and at least partially exposed to said surface sheet wherein said absorbent layer comprises 20 wt.% or more of a nodular fiber, said nodular fiber comprising a hydrophilic fiber having a wet to dry tenacity ratio of 80% or more.

2. The absorbent article as defined in claim 1, wherein said absorbent layer comprises 50 wt.% or more of said nodular fiber.

3. The absorbent article as defined in claim 1, wherein said nodular fiber comprises a skeletal fiber selected from the group consisting of polyester, polypropylene, polyethylene, polyvinyl chloride, polyvinylidiene chloride, nylon, acrylic, cotton, and flax fibers.

4. The absorbent article as defined in claim 1, wherein said nodular fiber has a fiber size of about 1.5 to 6 deniers.

5. The absorbent article as defined in claim 1, wherein said nodular fiber comprises a skeletal fiber that is partially heat fused or partially bonded with a binder.

6. The absorbent article as defined in claim 1, wherein said nodular fiber is disposed on the surface of said absorbent layer adjacent to said liquid-permeable surface sheet.

7. The absorbent article as defined in claim 1, wherein said absorbent layer comprises nodular fiber mixed with other hydrophilic fiber, said nodular fiber being disposed throughout said absorbent layer.

8. The absorbent article as defined in claim 1, wherein said absorbent layer comprises only said nodular fiber.

9. The absorbent article as defined in claim 1, wherein said absorbent article comprises a sanitary napkin, a disposable diaper, or a pad for incontinence.

10. The absorbent article as defined in claim 9, wherein said absorbent article comprises a sanitary napkin, a disposable diaper, or a pad for incontinence.

11. The absorbent article as defined in claim 1, wherein said nodular fiber comprises a skeletal fiber selected from the group consisting of polyester, polyester/polypropylene conjugate fibers, and polyester/-polyethylene conjugate fibers.

12. The absorbent article as defined in claim 11, wherein said nodular fiber has a fiber size of about 1.5 to 6 deniers.

13. The absorbent article as defined in claim 12, wherein said nodular fiber has a length of from 1 mm to 6 mm.

14. The absorbent article as defined in claim 12, wherein said nodular fiber comprises a skeletal fiber that is partially heat fused or partially bonded with a binder.

15. The absorbent article as defined in claim 14, wherein said nodular fiber has a length of from 1 mm to 6 mm.

16. The absorbent article as defined in claim 15, wherein said absorbent layer comprises nodular fiber mixed with other hydrophilic fiber, said nodular fiber being disposed throughout said absorbent layer.

17. The absorbent article as defined in claim 15, wherein said absorbent article exhibits liquid absorption, compression resistance, and deformation recovery characteristics so as to prevent liquid back flow and wilting.

18. The absorbent article as defined in claim 15, wherein said nodular fiber is disposed on the surface of said absorbent layer adjacent to said liquid-permeable surface sheet.

19. The absorbent article as defined in claim 18, wherein said absorbent article comprises a sanitary napkin, a disposable diaper, or a pad for incontinence.

20. The absorbent article as defined in claim 15, wherein said absorbent layer comprises only said nodular fiber.

21. The absorbent article as defined in claim 20, wherein said absorbent article comprises a sanitary napkin, a disposable diaper, or a pad for incontinence.

* * * * *